United States Patent [19]

Ambos

[11] Patent Number: 5,007,283
[45] Date of Patent: Apr. 16, 1991

[54] METHOD AND DEVICE FOR PROCESSING MEASURED VALUES

[75] Inventor: Stefan Ambos, Waiblingen, Fed. Rep. of Germany

[73] Assignee: Conducta Gesellschaft fur Meb-und Regeltechnik mbH & Co., Gerlingen, Fed. Rep. of Germany

[21] Appl. No.: 359,477

[22] Filed: May 31, 1989

[30] Foreign Application Priority Data

Jun. 4, 1988 [DE] Fed. Rep. of Germany ....... 3819101

[51] Int. Cl.$^5$ .................. G01N 27/04; G01D 18/00
[52] U.S. Cl. .................................. 73/1 G; 73/23.21; 324/608; 324/70 X; 364/571.02
[58] Field of Search .............. 73/1 G, 27 R, 27 A, 73/23, 23.2, 23.21; 364/571.01–571.08; 338/34, 35; 422/90; 324/601–611, 720, 721, 704

[56] References Cited

U.S. PATENT DOCUMENTS

| | | | |
|---|---|---|---|
| 3,418,914 | 12/1968 | Finkin | 73/27 R X |
| 3,429,178 | 2/1969 | Darbin | 73/27 R |
| 3,864,628 | 2/1975 | Klass et al. | 73/23 X |
| 4,147,513 | 4/1979 | Bienkawski et al. | 73/23 X |
| 4,151,738 | 5/1979 | Hyer et al. | 73/1 G |
| 4,156,181 | 5/1979 | Tears, Jr. | 324/720 X |
| 4,223,549 | 9/1980 | Kitzinger | 73/1 G X |
| 4,321,113 | 3/1982 | Granbow et al. | 73/1 G X |
| 4,326,414 | 4/1982 | Torada et al. | 324/720 X |
| 4,627,269 | 12/1986 | Forster et al. | 73/1 G X |
| 4,663,958 | 5/1987 | Matthiessen | 73/1 G |

FOREIGN PATENT DOCUMENTS

| | | |
|---|---|---|
| 3036106 | 4/1982 | Fed. Rep. of Germany ....... 73/1 G |
| 3140875 | 4/1983 | Fed. Rep. of Germany ....... 364/571.04 |
| 3504499 | 6/1986 | Fed. Rep. of Germany . |
| 163862 | 10/1982 | Japan ....... 73/1 G |
| 27849 | 2/1985 | Japan . |
| 256249 | 11/1986 | Japan ....... 73/1 G |
| 1191858 | 11/1985 | U.S.S.R. ....... 73/1 G |

OTHER PUBLICATIONS

*Patent Abstracts of Japan*; Grp P367, vol. 9, No. 151, ABS pub. date Jun. 26, 1985 (60-27849).

*Primary Examiner*—Tom Noland
*Attorney, Agent, or Firm*—Darby & Darby

[57] ABSTRACT

In connection with a method and a device for processing measured values, where resistance variations are evaluated as a measure for the variation of the gas concentration to be measured, it is proposed to measure a basic resistance value at least once, preferably repeatedly, by admitting a standard calibration gas, and to store this resistance value and derive therefrom, for each subsequent measurement of the gas component the concentration of which is to be measured, by an arithmetic operation, the ratio between the resulting total resistance value and the momentary basic resistance value, and to evaluate the ratio so obtained for further processing.

6 Claims, 2 Drawing Sheets

METHOD AND DEVICE FOR PROCESSING MEASURED VALUES

BACKGROUND OF THE INVENTION

In gas analysis, sensors are in use for determining the concentration of gases, more generally for detecting risks when working with microwaves, for smoke and fire detection, and the like, which consist of sensor elements in the form of semiconductors or specially processed resistors varying their resistance value in response to the value to be measured, i.e. especially in response to the gas concentration to be measured.

In the case of these known methods for processing measured values, i.e. especially when semiconductor sensors are used as measure for the gas concentration to be measured—and this is the application which will be described in more detail below because it is the preferred application of the present invention although the latter is not restricted to it—the indication of the gas concentration measured is derived from the varying resistance value which will be described hereafter by RS. However, such a sensor which varies its resistance value in response to the value to be measured is not capable of starting at a resistance value of zero when the concentration is equal to zero, for example; instead, the respective semiconductor sensor has a basic resistance value Ro which will initially be regarded hereafter as a constant value, but this only with respect to the gas concentration to be measured, as this basic resistance is in fact dependent on many other factors and may be subject to foreign influences external to the measurement proper.

So, the value normally measured is the sum of the basic resistance Ro plus the resistance portion $\Delta RS$ which leads to the aggregate resistance RS.

The basic resistance value Ro may vary for certain sensor types, due to production reasons, between 5 kOhm and 15 kOhm and may, in addition to these wide variations, be dependent on the existing air humidity, angle and velocity of flow, aging phenomena, long-term stability and may also, under certain circumstances, be heavily influenced by temperature changes. When evaluating measurements taken, on the basis of the total resistance value assumed at any time by the semiconductor sensor, for example when measuring varying gas concentrations, these parameters will be contained in the results of the measurement as measuring errors or must be corrected and considered (later) by troublesome processes. To this effect, it will frequently be necessary to determine at least the temperature prevailing at the place of measurement so that it can be considered in evaluating the measured resistance values.

Now, it is the object of the present invention to provide a method and a device for processing measured values where any additional factors influencing the values determined by a sensor which varies its resistance value are minimized or even completely eliminated.

ADVANTAGES OF THE INVENTION

The invention solves this problem with the aid of the characterizing features of the main claim and/or of subclaim 4 and provides the advantage that it is now possible to obtain very exact measured values even with the aid of low-cost (semiconductor) sensors, which accordingly exhibit wide variations of their basic resistance value, and that the undesirable influences resulting from the basic resistance value and occurring mainly with respect to the latter, will no longer make themselves felt in a notable manner.

The invention, therefore, succeeds in eliminating the different influences to which the basic resistance Ro is exposed, Ro being exactly that resistance value which is not influenced by the gas concentration to be measured. The invention elminates product variations, production tolerances and any deviations developing over time during the measurements, i.e. aging phenomena, all of them being disturbing variables which are finally reflected as errors by the measuring result when the measurement is conducted with the pure resistance value RS.

It is a further advantage of the invention that for carrying out (repeated) checks of the Ro resistance value—which checks may be performed, for example, according to a predetermined calibration rhythm—the calibration need not necessarily be effected using the same gas whose concentration is to be determined. Rather, such calibration may be carried out for all measuring components to be determined by such semiconductor sensors, or even sensors of different designs, with the aid of any standard calibration gas of lower concentration, such as methane, propane, butane, or the like.

The features described by the subclaim permit advantageous improvements and developments of the invention. According to a particularly advantageous variant, the basic resistance value Ro is stored repeatedly by repeated calibration within predetermined periods of time so that following every such calibration the newly determined Ro resistance value may be used, which also helps improve considerably the zero-point stability of the measuring system.

BRIEF DESCRIPTION OF THE DRAWING

One embodiment of the invention will be described hereafter with reference to the drawing.

DESCRIPTION OF THE EMBODIMENTS

Figure 1:
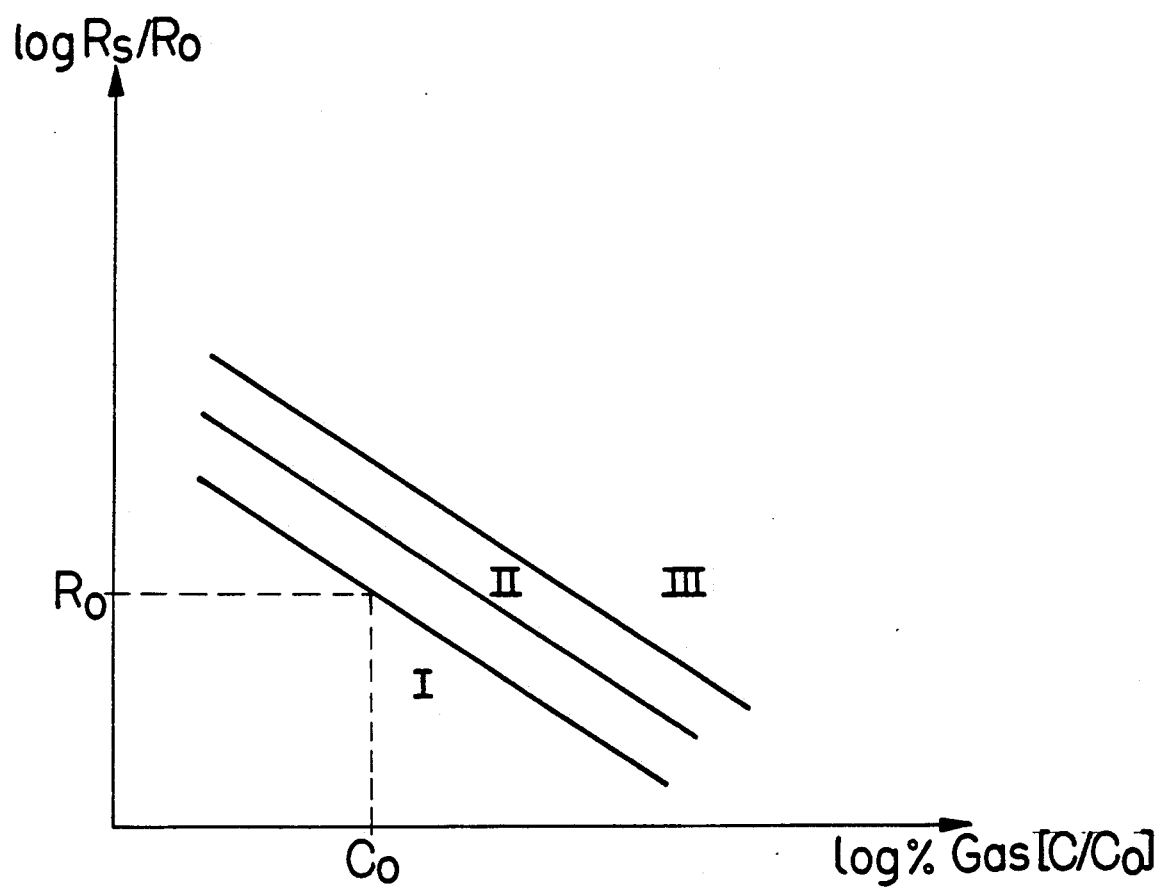
FIG. 1 illustrates by way of a diagram the variation of the curve patterns of semiconductor sensors of the same type, which exhibit great differences in their basic resistance value as a result of production factors, aging and environmental conditions, and further the curve patterns obtained for varying gas concentrations.

The basic idea of the invention is seen in the fact that although one still uses the entire resistance value of the (semiconductor) sensor for measuring gas concentrations—in fact, it would not seem possible to proceed otherwise as the sensor is to be regarded as one unit—one now determines the basic resistance value Ro in advance and has the indication of the measured value preceded by an arithmetic operation by which one determines the relation of the measured value RS to the basic resistance value Ro.

The curve patterns I, II and III illustrate the interdependence between certain signal or measuring resistances Rs and the gas concentration of the respective gas component to be measured, the differences between the parallel curve patterns being due to differences in the absolute resistance values Ro.

According to the present invention, the measured value of a gas concentration to be measured is always evaluated as the ratio between Rs/Ro. To this end, a first (calibration) measurement is carried out by which the semiconductor sensor is subjected to the influence of air or—and this has been found to be particularly practical—to a standard calibration gas of any concentration, for determining the basic resistance value Ro. The standard calibration gas may be used for any measuring components as variations of the ration Rs/Ro resulting from aging phenomena or environmental conditions will always be identical for all measuring components of a sensor.

The basic resistance value Ro so determined is stored and taken as a basis for all subsequent measurements of the gas concentration, which means that the varying values of Rs are always related to the basic resistance value Ro so determined.

It is advisable to have the basic resistance value RO measured automatically by means of a suitable gas detection system, at a predetermined calibration rhythm of, for example, three months, using the standard calibration gas or air, and to store the basic resistance value measured last as a corrected new value. This repeated measurement of the Ro value effected at predetermined time intervals eliminates any variations due to aging phenomena and ensures perfect measurements for the next calibration interval.

The relation Rs/Ro then taken as a basis for determining the actual measured value will then remain constant (for a constant gas concentration) and will not be influenced by any of the factors mentioned before so that it will then be possible to build up reliable and precise measuring systems even with cheap semiconductor sensors. The new Ro values determined on the occasion of each calibration of the gas sensor and stored for the coming arithmetic operations also lead to a considerably improved zero-point stability.

For calibrating and determining the basic resistance value Ro, it has been found to be advantageous to use a standard calibration gas having a concentration of, for example, 3000 ppm methane ($CH_4$) instead of air. One obtains in this manner a defined value in the Ro calibration process.

Figure 2:
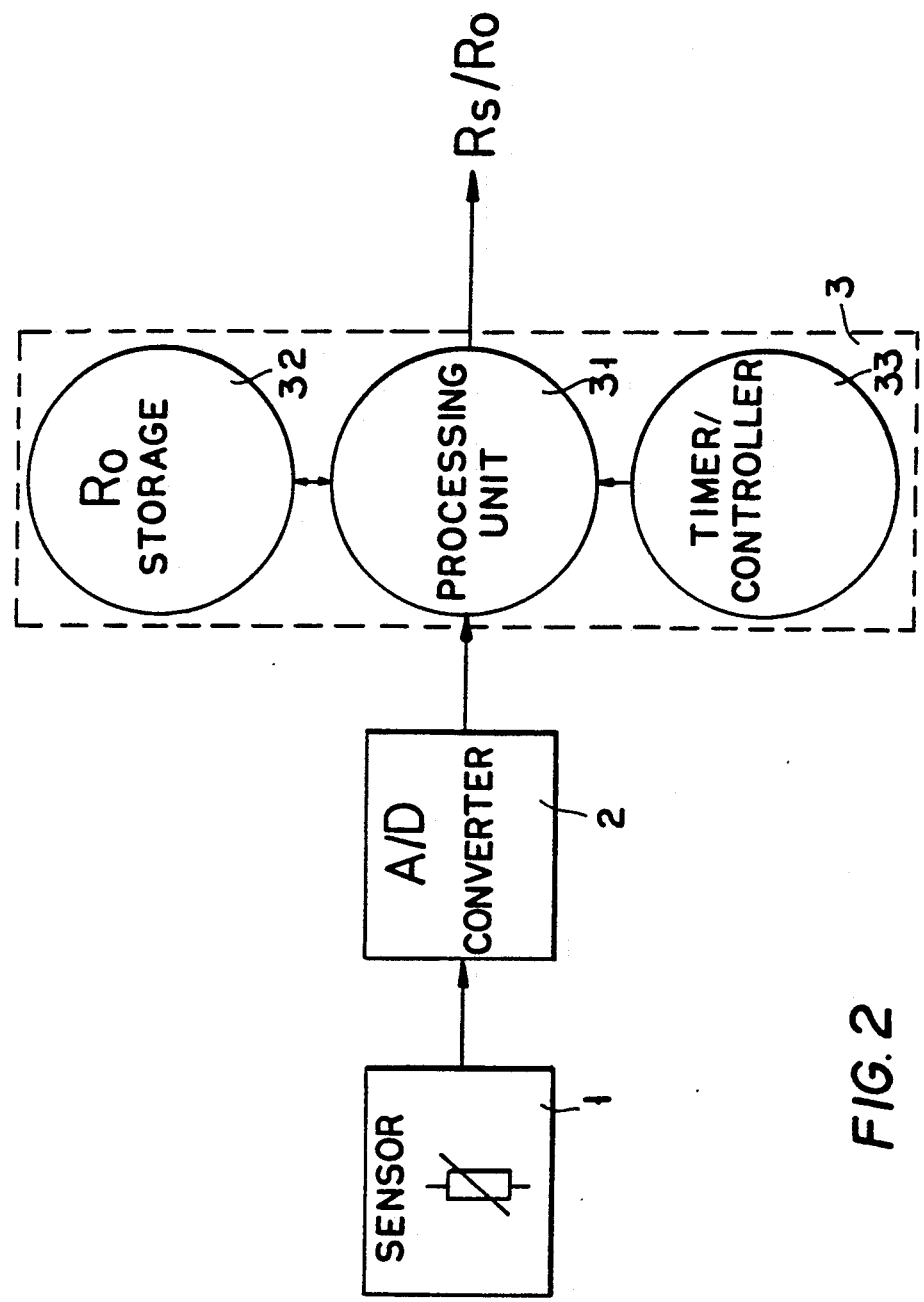
FIG. 2 is a functional diagram of an apparatus in accordance with the invention for practicing the method of the invention.

An apparatus for practicing the method of the invention is illustrated in FIG. 2. The apparatus includes a sensor 1, represented by a variable resistor that varies in resistance in response to the concentration of the gas to be measured. The instantaneous resistance is transformed into a suitable electrical analog signal, which is converted into digital format by the analog to digital converter 2. A computer 3, or more often, a microcontroller, receives resistance signal data, in particular data representing Ro and Rs, respectively, and calculates the ration Rs/Ro and delivers a digital representation of this ratio value for further processing. Rs and Ro have been defined above.

The functions of the computer 3 may be partly represented by hardware and partly by software in actual practice. A processing unit 31 receives the data samples from the sensor 1. The Ro value, that is, based upon a concentration that excludes the presence of the gas to be measured, is stored in a memory or storage 32. A timer 33 regularly triggers the sampling of new Rs values that vary according to the actual gas concentration to be measured. The Rs/Ro ratio calculation is then performed by the processing unit 31 using the actual Rs value and the stored Ro value. Periodically, as determined by the timer controller 33, new values for Ro may be obtained and stored in memory 32 to displace the original values of Ro.

All features mentioned or shown in the above description, the following claims and the drawing may be essential to the invention either alone or in any combination thereof.

I claim:

1. A method for processing measured values in a gas detection device evaluating a resistance variation of a gas sensor forming part of said device for a range of gas concentrations to be measured, comprising the steps of determining and storing at least once a basic resistance value (Ro) of said, without the influence of the gas to be measured, and determining for every subsequent measurement of the gas component, the concentration of which is to be measured, the ratio between a resulting total resistance value (Rs) of said gas sensor dependent on gas concentration and the basic resistance value (Ro), by an arithmetic operation, and using thereafter the value (Rs/Ro) so obtained.

2. A method according to claim 1, wherein the basic resistance value (Ro) is repeatedly measured at predetermined time intervals and stored as a new basic resistance value (Ro) which is then used for deriving said ratio.

3. A method according to claim 2, wherein a standard calibration gas is used for effecting said repeated measurement and subsequent storage of the new basic resistance value (Ro) and the total resistance values (Rs) determined thereafter are related to the new basic resistance value (Ro) so determined.

4. A method according to claim 3, wherein said calibration gas is 3,000 ppm $CH_4$.

5. A device for processing measured values in a gas detection device evaluating resistance variations for a gas concentration to be measured, comprising a storage in which a basic resistance value (Ro) of a sensor having a resistance that varies with gas concentration, is stored before measuring the total resistance value Rs of the sensor and circuit means for deriving the ratio between every new measured total resistance value (Rs) of the sensor and the basic resistance value (Ro) stored at any time, and for outputting this ratio for further processing.

6. A device as in claim 4, wherein said sensor is a semiconductor sensor.

* * * * *